(12) United States Patent
Choudary et al.

(10) Patent No.: US 6,673,967 B1
(45) Date of Patent: Jan. 6, 2004

(54) METHOD OF PROCESSING OF HYDROGEN FOR REDUCTIVE ACYLATION OF NITRO, AZIDO AND CYANO ARENES

(75) Inventors: Boyapati Manoranjan Choudary, Andhra Pradeah (IN); Venkati Sri Ranganath Kalluri, Andhra Pradeah (IN); Lakshmi Kantam Mannepalli, Andhra Pradeah (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/306,844

(22) Filed: Nov. 29, 2002

(51) Int. Cl.⁷ ................. C07C 231/06; C07C 231/10
(52) U.S. Cl. ................. 564/124; 564/143; 564/218; 549/69; 562/452
(58) Field of Search ................. 564/124, 143, 564/218; 549/69; 562/452

(56) References Cited
U.S. PATENT DOCUMENTS 6,215,024 B1 * 4/2001 Choudary et al. .......... 564/138

FOREIGN PATENT DOCUMENTS

EP 1090907 A1 4/2001

OTHER PUBLICATIONS

Lee et al., "One–Pot Conversion of Nitroarenes into N–Arylamides" Bulletin of the Korean Chemical Society, vol. 23, No. 10, Oct. 20, 2002, pp. 1359–1360, XP009013989.

Kamal et al, "An Efficient Reduction of Azides to Amines:Synthesis of DNA Interactive pyrrolo'2,1–c!' 1,4!benzodiazepines", Tetrahedron Letters, vol. 41, Sep. 30, 2000, pp. 7743–7746, XP004217740.

* cited by examiner

*Primary Examiner*—Shailendra Kumar
(74) *Attorney, Agent, or Firm*—Nixon & Vanderhye P.C.

(57) ABSTRACT

A method for processing of hydrogen for the reductive acylation of nitro, azido and cyano arenes is disclosed. More particularly, improved process for the preparation of amides and anilides using $C_3$–$C_7$ carboxylic acids as proton source/acylating agents employing $Fe^{3+}$-montmorillonite as a catalyst is disclosed.

25 Claims, No Drawings

US 6,673,967 B1

METHOD OF PROCESSING OF HYDROGEN FOR REDUCTIVE ACYLATION OF NITRO, AZIDO AND CYANO ARENES

FIELD OF THE INVENTION

The present invention relates to a method for processing of hydrogen for the reductive acylation of nitro, azido and cyano arenes. More particularly, this invention relates to an improved process for the preparation of amides and anilides using $C_3$–$C_7$ carboxylic acids as proton source/acylating agents employing $Fe^{3+}$-montmorillonite as a catalyst.

This invention particularly relates to an eco-friendly process for reductive acylation of nitro, azido and cyano arenes using metal cation exchanged montmorillonite as a catalyst dispensing with the use of stiochiometric amounts of corrosive salts as reagents. The reductive acylated products are important intermediates in the preparation of drugs and pharmaceuticals.

BACKGROUND OF THE INVENTION

Reference is made to Li et al., *Journal of American Chemical Society*; 726,124,2002 wherein enzymes are known to produce and consume hydrogen. The inherent disadvantages in this process are the electrons are supplied by H-clusters.

Reference is made to Cammack, *Nature*; 214, 397, and 1999 wherein [Fe]-hydrogenase enzyme is known to produce hydrogen, while the [Ni-Fe]-hydrogenase consumes hydrogen. The inherent disadvantages in this process are complex and tedious synthetic protocols. The hydrogenase models are developed to produce hydrogen substoichiometrically.

Reference is made to Nomura, *Journal of Molecular Catalysis A.*, 1, 130, 1998 wherein reduction of nitroarenes is carried out using carbonyl complexes as catalysts under carbon monoxide pressures. The inherent disadvantage in this process is the use of non-regenerable expensive carbonyl complexes in stoichiometric quantities or expensive catalysts with hydrogen or CO pressure.

Reference is made to Wantanabe et al; *Journal of Organic Chemistry* 4451, 49, 1984 wherein reductive acylation of nitrobenzene is carried out by using platinum complexes under carbon monoxide pressure. The inherent disadvantages in this process are use of expensive platinum complexes and high CO pressure.

Reference is made to Kamal et al; *Tetrahedron Letters*, 7743, 41, 2000 wherein azides are reduced to amines by using stiochiometric quantities of $FeSO_4$ in ammonia solution. The major drawback in this process is the reduction of azo compounds induced by non-regenerable stoichiometric hydride reagents.

OBJECTS OF THE INVENTION

The main object of the present invention is to provide a method for the processing of hydrogen for the reductive acylation of substituted nitro, azido and cyano arenes which obviates the drawbacks detailed above.

It is another object of the present invention to provide a novel and ecofriendly process for the production and consumption of hydrogen for the reductive acylation of substituted nitro, azido and cyano arenes.

It is a further object of the invention to provide a novel, economic and ecofriendly process for the reductive acylation of nitro, azido and cyano compounds.

It is yet another object of the invention to provide a process for the reductive acylation of substituted nitro, azido and cyano arenes which dispenses with the use of corrosive and stiochiometric quantities of non-regenerable expensive carbonyl complexes in stiochiometric quantities or expensive catalysts with hydrogen or CO pressure.

It is yet another object of the invention to provide a process for the reductive acylation of substituted nitro, azido and cyano arenes with good selectivity and yields.

It is yet another object of the invention to provide a process for the reductive acylation of substituted nitro, azido and cyano arenes wherein the catalyst can be recycled without significant loss of activity.

SUMMARY OF THE INVENTION

The novelty of the present invention provides resides in the production of hydrogen and consumption in the reductive acylation of nitro, azido, and cyano compounds using carboxylic acid as a proton source/acylating agents and iodide anion as electron source by metal exchanged montmorillonite catalyst under reflux conditions.

Promotive effect of montmorillonite, a prebiotic material and low redox potential of iron, and abundance of both these materials at cheaper cost prompted its use in the present studies. Higher yields and selectivities are obtained towards amides and anilides, when $Fe^{3+}$-montmorillonite as synthesized is used in the reductive acylation of nitro, azido and cyano arenes in carboxylic acid solvent. Since anilides and amides are the desired starting materials for the synthesis of drugs, pharmaceuticals, this invention is timely and appropriate. Thus earlier papers, patents fell short of expectations for commercial reality and economics of the process. Thus, this invention offers the best techno-economic route for the synthesis of amides and anilides intermediates for drugs and pharmaceuticals.

Accordingly, the present invention provides a method for the processing of hydrogen used in the reductive acylation of nitro, azido, and cyano arenes comprising reacting $C_3$–$C_7$ carboxylic acid as an acylating agent/proton source and iodide as electron source using metal exchanged montmorillonite as a catalyst at a temperature in the range of 116–200° C. for a time period in the range of 0.5–24 h, recovering the catalyst by filtration for reuse and recovering the acylated product.

In an embodiment of the invention, the processing of hydrogen comprises production of hydrogen at room temperature and consumption of hydrogen at higher temperatures.

In an embodiment of the invention, the temperature used for simultaneous production and consumption in the reductive acylation of substituted nitro, azido and cyano arenes is in the range of 25–200° C.

In an embodiment of the invention, the metal ion used for exchange on montmorillonite is selected from the group consisting of $Fe^{3+}$, $Cu^{2+}$, $Ce^{3+}$, $Zr^{4+}$ and $Al^{3+}$ In an embodiment of the invention, the production and consumption of hydrogen is catalysed by the same catalyst.

In an embodiment of the invention, the production of hydrogen is by the reduction of proton generated from the carboxylic acid.

In another embodiment of the invention, the reduction of proton generated from carboxylic acid is effected at room temperature by $M^{n+}$-montmorillonte where $M^{n+}$ is selected from $Fe^{3+}$, $Cu^{2+}$, $Ce^{3+}$, $Zr^{4+}$ and $Al^{3+}$.

In another embodiment of the invention the nitro, azido or cyano arenes used for the reductive acylation reactions comprise substituted aromatic compounds selected from the group consisting of methyl, ethyl, propyl, halogen, acid, aryl and heteroaryl.

In yet another embodiment of the invention, the quantity of the catalyst is 5 to 20% by weight with respect to the substrate.

In another embodiment of the invention the $C_3$–$C_7$ carboxylic acid is selected from the group consisting of propionic acid to heptanoic acid.

In another embodiment of the invention, the iodide anion used as electron source is sodium iodide.

In another embodiment of the invention, the ratio of nitro, azido or cyano compounds to acylating agent is 1:4 to 1:8

In a further embodiment of the invention, the ratio of nitro and azido compounds to sodium iodide is 1:2 to 1:6

In yet another embodiment of the invention the ratio of cyano compounds to sodium iodide is 1:3 to 1:6

In another embodiment of the invention, the reaction of nitro and cyano compounds is effected at a temperature of 160–200° C.

In another embodiment of the invention, the reaction of azido compounds is effected at a temperature of 116–160° C.

In still another embodiment of the present invention, the reaction is effected for a period of 0.5–24 hrs.

DETAILED DESCRIPTION OF THE INVENTION

The invention provides a method for the processing of hydrogen for the reductive acylation of substituted nitro, azido and cyano arenes, by reacting $C_3$–$C_7$ carboxylic acids as acylating agents/proton sources, iodide ion as electron source, employing metal cation exchanged montmorillonite as catalyst generally at a temperature in the range of 116–200° C. for a period of 0.5–24 h, and recovering the catalyst by filtration for re-use and the acylated products by conventional methods. The processing of hydrogen comprises production of hydrogen at room temperature and consumption of hydrogen at higher temperatures. Generally, both the production and consumption of hydrogen is catalysed by the same catalyst. Hydrogen is produced by the reduction of proton generated from carboxylic acid.

The process of the invention dispenses with the use of corrosive and non-regenerable stoichiometric hydride reagents or under hydrogen pressure in the presence of expensive catalysts, and non-regenerable expensive carbonyl complexes in stoichiometric quantities or using expensive catalysts with hydrogen or CO pressure.

Another object of the present invention is to provide a process for the preparation of amides and anilides wherein the selectivity and conversions are good and the work up procedure is simple. The reduction of proton generated from carboxylic acid is effected at room temperature by $M^{n+}$-montmorillonte catalyst where $M^{n+}$ is preferably $Fe^{3+}$, $Cu^{2+}$, $Ce^{3+}$, $Zr^{4+}$, or $Al^{3+}$. The montmorillonite or metal exchanged montmorillonite are used as catalysts for the reductive acylation of nitro, azido, and cyano arenes. The catalyst can be used for several cycles with consistent activity.

The $C_3$–$C_7$ carboxylic acids used as acylating agents/proton sources are preferably selected from propionic acid to heptanoic acid. Sodium iodide is a preferred electron source. In an embodiment of the present invention, the temperature used for simultaneous production and consumption of hydrogen in the reductive acylation of substituted nitro, azido and cyano arenes is in the range of 25–200° C. The nitro, azido, cyano arenes used for the reductive acylation reactions are substituted aromatic compounds selected from methyl, ethyl, propyl, halogen, acid, aryl and heteroaryl.

The quantity of the catalyst is 5 to 20% by weight with respect to the substrate. The ratio of nitro, azido and cyano compounds to acylating agent is preferably 1:4 to 1:8. More particularly, the ratio of nitro and azido compounds to sodium iodide is preferably 1:2 to 1:6 and the ratio of cyano compounds to sodium iodide is 1:3 to 1:6. The reaction of nitro and cyano compounds is preferably effected at a temperature of 160–200° C. and the reaction of the azido compounds is effected at a temperature of 116–160° C.

The following examples are given by way of illustration of the present invention and therefore should not be construed to limit the scope of invention.

EXAMPLE 1

Catalyst Preparation a) Metal exchanged-montmorillonite:

K 10-montmorillonite purchased from Fluka chemicals was used as such. To a 1-liter solution of $FeCl_3$ chloride (1.0 M), 80 g of K 10 montmorillonite was added. Stirring was maintained for 24 h in order to saturate the exchange capacity of montmorillonite K 10. The clay suspension was centrifuged and the supernatant solution was discarded. The clay catalyst was washed each time with fresh distilled water and centrifuged till the disappearance of chloride ions from the discarded water. The clay was dried overnight in an oven at 120 degree. C and finally ground in a mortar.

b) $Zn^{2+}$-exchanged catalyst:

It was prepared in the same manner as in example a, stirring 1M solution of $ZnCl_2$ and 80 g of K10 montmorillonite.

c) $Ce^{3+}$-exchanged catalyst:

It was prepared in the same manner as in example a, stirring 1M solution of $CeCl_3$ and 80 g of K10 montmorillonite.

d) $Cu^{2+}$-exchanged catalyst:

It was prepared in the same manner as in example a, stirring 1M solution of $CuCl_2$ and 80 g of K10 montmorillonite.

e) $Al^{3+}$-exchanged catalyst:

It was prepared in the same manner as in example a, stirring 1M solution of $AlCl_3$ and 80 g of K10 montmorillonite.

EXAMPLE 2

A mixture of propionic acid (10 ml), sodium iodide (3.0 g, 20 mmol) and $Fe^{3+}$-montmorillonite catalyst (0.5 g) were stirred in a round-bottomed flask at 25° C. for 6 h. The reaction mixture was filtered off to separate the catalyst. The resultant filtrate was titrated with 0.1M sodium thiosulphate solution using starch as an indicator to know the amount of iodine present in the solution. The amount of iodine liberated in the reaction is 0.998 g (3.7 mmol)

EXAMPLE 3

A mixture of acetic acid 10 ml, sodium iodide (20 mmol) and $Fe^{3+}$-montmorillonite catalyst (0.5 g) were stirred in a round-bottomed flask (50 ml) at reflux temperature. After obtaining temperature, 2-azido anisole, (10 mmol) were added slowly drop by drops for ten minutes and continued the reaction. After completion of the reaction (followed by G.C), the reaction mixture was filtered and to separate the catalyst. The reaction mixture was taken into ethyl acetate, quenched with sodium thiosulphate and washed with sodium bicarbonate to remove unreacted acid and distilled off to obtain the product. Yield: 1.61 g

EXAMPLES 4–7

The procedure was followed as in example 3, with various substrates and results are shown in Table 1

EXAMPLE 8

A mixture of propionic acid (40 mmol), sodium iodide (30 mmol) and $Fe^{3+}$-montmorillonite catalyst (0.5 g) were stirred in a round-bottomed flask (50 ml) at reflux temperature. After obtaining temperature benzonitrile, (10 mmol) was added slowly drops by drop for ten minutes and continued the reaction. After completion of the reaction (followed by G.C), the reaction mixture was filtered to separate the catalyst. The reaction mixture was taken into ethyl acetate, quenched with sodium thiosulphate and washed with sodium bicarbonate to remove unreacted acid and distilled off to obtain crude product. Yield: 1.14 g

EXAMPLES 9–11

The procedure was followed as in example 8, with various substrates and results are shown in Table 1

EXAMPLE 12

A mixture of propionic acid (10 ml), sodium iodide (20 mmol) and $Fe^{3+}$-montmorillonite catalyst (0.5 g) were stirred in a round-bottomed flask (50 ml) at reflux temperature (160° C.). After obtaining temperature nitrobenzene (10 mmol) were added slowly drop by drops for ten minutes and continued the reaction. After completion of the reaction (followed by G.C), the reaction mixture was filtered off to separate the catalyst. The reaction mixture was taken into ethyl acetate, quenched with sodium thiosulphate and washed with sodium bicarbonate to remove unreacted acid and distilled off to obtain product. Yield: 1.19 g

EXAMPLES 13–21

Procedure was followed as in example 12, with various substrates. Results are shown in Table 1

TABLE 1

Reductive N-acylation of nitro, cyano and azido compounds using $Fe^{3+}$-montmorillonite as a catalyst.

| Example | Substrate | Time (h) | Yield[a] (%) |
| --- | --- | --- | --- |
| 3 | 2-azidoanisole | 0.50 | 98 |
| 4 | 4-azidonitrobenzene | 0.50 | 98 |
| 5 | 4-azidochlorobenzene | 0.50 | 100 |
| 6 | 4-azidoanisole | 0.50 | 85 |
| 7 | 2-azidobenzoic acid | 0.50 | 92 |
| 8 | Benzonitrile | 20 | 70 |
| 9 | o-cyanotoluene | 20 | 40 |
| 10 | p-methoxybenzonitrile | 20 | 50 |
| 11 | p-chlorobenzonitrile | 20 | 60 |
| 12 | Nitrobenzene | 12 | 82 |
| 13 | p-nitroanisole | 12 | 74 |
| 14 | o-nitroanisole | 12 | 73 |
| 15 | p-bromonitrobenzene | 12 | 70 |
| 16 | p-chloronitrobenzene | 16 | 63 |
| 17 | o-nitrotoluene | 12 | 76 |
| 18 | p-nitrotoluene | 12 | 75 |
| 19 | m-nitrotoulene | 12 | 70 |
| 20 | 1-nitronaphthalene | 12 | 70 |

TABLE 1-continued

Reductive N-acylation of nitro, cyano and azido compounds using $Fe^{3+}$-montmorillonite as a catalyst.

| Example | Substrate | Time (h) | Yield[a] (%) |
| --- | --- | --- | --- |
| 21 | 2-nitrothiophene | 12 | 75 |

[a]Yields by G.C analysis.

The main advantages of the present invention are:
1. A novel and ecofriendly process for the production and consumption of hydrogen.
2. A novel and ecofriendly process for the reductive acylation of nitro, azido and cyano compounds.
3. The present process dispenses the use of corrosive and stiochiometric quantities of non-regenerable expensive carbonyl complexes in stiochiometric quantities or using expensive catalysts with hydrogen or CO pressure.
4. The cheaply and readily available metal exchanged montmorillonite as a catalyst for the reductive acylation.
5. The selectivity and yields are good.
6. The present process envisages no disposal problem as the catalyst can be used for several cycles. The catalyst was subjected to many recycles, which displayed consistent activity
7. The present process is environmentally safe since there is no disposal problem.
8. The process is economical.

We claim:
1. A method for the processing of hydrogen used in the reductive acylation of nitro, azido, and cyano arenes comprising reacting $C_3$–$C_7$ carboxylic acid as an acylating agent/proton source and iodide as electron source using metal exchanged montmorillonite as a catalyst at a temperature in the range of 116–200° C., recovering the catalyst by filtration for reuse and recovering the acylated product.

2. A method as claimed in claim 1 wherein the processing of hydrogen comprises production of hydrogen at room temperature and consumption of hydrogen at higher temperatures.

3. A method as claimed in claim 1 wherein the temperature used for simultaneous production and consumption of hydrogen in the reductive acylation of substituted nitro, azido and cyano arenes is in the range of 25–200° C.

4. A method as claimed in claim 1 wherein the metal ion used for exchange on montmorillonite is selected from the group consisting of $Fe^{3+}$, $Cu^{2+}$, $Ce^{3+}$, $Zr^{4+}$ and $Al^{3+}$.

5. A method as claimed in claim 1 wherein the production and consumption of hydrogen is catalysed by the same catalyst.

6. A method as claimed in claim 1 wherein the production of hydrogen is by the reduction of proton generated from the carboxylic acid.

7. A method as claimed in claim 6 wherein the reduction of proton generated from carboxylic acid is effected at room temperature by $M^{n+}$-montmorillonte where $M^{n+}$ is selected from $Fe^{3+}$, $Cu^{2+}$, $Ce^{3+}$, $Zr^{4+}$ and $Al^{3+}$.

8. A method as claimed in claim 1 wherein the nitro, azido or cyano arenes used for the reductive acylation reactions comprise substituted aromatic compounds selected from the group consisting of methyl, ethyl, propyl, halo, acid, aryl and heteroaryl.

9. A method as claimed in claim 1 wherein the quantity of the catalyst is 5 to 20% by weight with respect to the substrate.

10. A method as claimed in claim 1 wherein the $C_3$–$C_7$ carboxylic acid is selected from the group consisting of propionic acid to heptanoic acid.

11. A method as claimed in claim 1 wherein the electron source is sodium iodide.

12. A method as claimed in claim 1 wherein the ratio of nitro, azido or cyano compounds to acylating agent is 1:4 to 1:10.

13. A method as claimed in claim 12 wherein the ratio of nitro and azido compounds to sodium iodide is 1:2 to 1:6.

14. A method as claimed in claim 12 wherein the ratio of cyano compounds to sodium iodide is 1:3 to 1:6.

15. A method as claimed in claim 1 wherein the reaction of nitro and cyano compounds is effected at a temperature of 160–200° C.

16. A method as claimed in claim 1 wherein the reaction of azido compounds is effected at a temperature of 116–160° C.

17. A method as claimed in claim 1 wherein the reaction is carried out for a period of 0.5–24 hrs.

18. A method as claimed in claim 1 wherein the catalyst is recycled several times with consistent activity.

19. A method as claimed in claim 1 wherein the nitro compound is nitrobenzene.

20. A method as claimed in claim 19 wherein the ratio of nitrobenzene to sodium iodide is 1:2 to 1:4.

21. A method as claimed in claim 14 wherein the cyano compound is a nitrile.

22. A method as claimed in claim 21 wherein the ratio of the nitrile compound to the sodium iodide is 1:3 to 1:6.

23. A method as claimed in claim 1 wherein the azido compound is an azide.

24. A method as claimed in claim 23 wherein the ratio of the azide compound to the sodium iodide is 1:2 to 1:4.

25. A method as claimed in claim 12 wherein the ratio of nitrobenzene, nitriles and azides to carboxylic acid is 1:4 to 1:10.

* * * * *